(12) United States Patent
Motegi et al.

(10) Patent No.: US 11,337,866 B2
(45) Date of Patent: May 24, 2022

(54) METHOD FOR MANUFACTURING ABSORBENT BODY

(71) Applicant: KAO CORPORATION, Tokyo (JP)

(72) Inventors: Tomoyuki Motegi, Ichikai-machi (JP); Yuki Kato, Utsunomiya (JP); Ryuji Matsunaga, Utsunomiya (JP); Takuaki Harada, Kaminokawa-machi (JP); Hiroyuki Iwasa, Tachikawa (JP)

(73) Assignee: KAO CORPORATION, Tokyo (JP)

( * ) Notice: Subject to any disclaimer, the term of this patent is extended or adjusted under 35 U.S.C. 154(b) by 158 days.

(21) Appl. No.: 16/608,429

(22) PCT Filed: Oct. 3, 2017

(86) PCT No.: PCT/JP2017/036035
§ 371 (c)(1),
(2) Date: Oct. 25, 2019

(87) PCT Pub. No.: WO2019/069384
PCT Pub. Date: Apr. 11, 2019

(65) Prior Publication Data
US 2020/0138636 A1  May 7, 2020

(51) Int. Cl.
*A61F 13/15* (2006.01)
*D04H 1/02* (2006.01)

(52) U.S. Cl.
CPC .. *A61F 13/15731* (2013.01); *A61F 13/15674* (2013.01); *A61F 13/15723* (2013.01);
(Continued)

(58) Field of Classification Search
None
See application file for complete search history.

(56) References Cited

U.S. PATENT DOCUMENTS 4,921,645 A  5/1990 Insley
5,456,982 A  10/1995 Hansen et al.
(Continued)

FOREIGN PATENT DOCUMENTS

CN  1426769 A   7/2003
CN  103948471 A  7/2014
(Continued)

OTHER PUBLICATIONS

Machine translation of WO 2017/038963 (Year: 2017).*
International Search Report, issued in PCT/JP2017/036035, dated Dec. 19, 2017.

*Primary Examiner* — Barbara J Musser
(74) *Attorney, Agent, or Firm* — Birch, Stewart, Kolasch & Birch, LLP

(57) ABSTRACT

A absorbent member manufacturing method of the invention is a method for manufacturing an absorbent member (100) including synthetic fibers (10*b*). The method involves: a transporting step of transporting a plurality of sheet fragments (10*bh*) including synthetic fibers (10*b*) to an accumulating depression (41) by using a duct 3; an accumulating step of accumulating, in the accumulating depression (41), the plurality of sheet fragments (10*bh*) transported in the transporting step, and forming an accumulation (100*a*') which is a constituent member of the absorbent member (100); and a pressing step of pressing the accumulation (100*a*') over its entirety in the thickness direction.

18 Claims, 6 Drawing Sheets

(52) U.S. Cl.
CPC ......... *A61F 13/15764* (2013.01); *D04H 1/02* (2013.01); *A61F 2013/15715* (2013.01); *D10B 2509/026* (2013.01)

(56) References Cited

U.S. PATENT DOCUMENTS

| | | | | |
|---|---|---|---|---|
| 2002/0147434 | A1* | 10/2002 | Mori | A61F 13/531 604/365 |
| 2003/0130639 | A1 | 7/2003 | Ishikawa et al. | |
| 2008/0300560 | A1 | 12/2008 | Magnusson et al. | |
| 2014/0182462 | A1 | 7/2014 | Hoshika | |
| 2014/0308483 | A1* | 10/2014 | Li | A61F 13/536 428/167 |
| 2019/0083324 | A1* | 3/2019 | Venturino | A61F 13/15658 |

FOREIGN PATENT DOCUMENTS

| | | | | |
|---|---|---|---|---|
| CN | 105007873 | A | 10/2015 | |
| EP | 0 389 023 | A2 | 9/1990 | |
| EP | 2 859 868 | A1 | 4/2015 | |
| JP | 3-504144 | A | 9/1991 | |
| JP | 2002-301105 | A | 10/2002 | |
| JP | 2008-113857 | A | 5/2008 | |
| JP | 2012-147997 | A1 | 8/2012 | |
| JP | 2012-213516 | A | 11/2012 | |
| JP | 2014-108319 | A | 6/2014 | |
| JP | 2016-104054 | A | 6/2016 | |
| JP | 2019-63367 | A | 4/2019 | |
| JP | 2019-63368 | A | 4/2019 | |
| JP | 2019-63369 | A | 4/2019 | |
| JP | 2019-63370 | A | 4/2019 | |
| JP | 2019-63371 | A | 4/2019 | |
| JP | 2019-63372 | A | 4/2019 | |
| JP | 2019-63374 | A | 4/2019 | |
| JP | 2019-63375 | A | 4/2019 | |
| JP | 2019-97613 | A | 6/2019 | |
| JP | 2019-97614 | A | 6/2019 | |
| JP | 2019-170952 | A | 10/2019 | |
| JP | 6591136 | B2 | 10/2019 | |
| RU | 2 389 511 | C2 | 5/2010 | |
| TW | 201402098 | A | 1/2014 | |
| WO | WO 2012/132460 | A1 | 10/2012 | |
| WO | WO-2017038963 | A1 * | 3/2017 | ............. A61F 13/15 |
| WO | WO 2019-069383 | A1 | 4/2019 | |

\* cited by examiner

METHOD FOR MANUFACTURING ABSORBENT BODY

TECHNICAL FIELD

The present invention relates to a method for manufacturing an absorbent member.

BACKGROUND ART

A known example of an absorbent member used in an absorbent article, such as a disposable diaper, a sanitary napkin or an incontinence pad, is an absorbent member including pulp fibers and synthetic fibers. Patent Literature 1 is a known example describing a method for manufacturing an absorbent member including pulp fibers and synthetic fibers.

Patent Literature 1 describes a method for manufacturing an absorbent member for an absorbent article, the method involving: shaping a nonwoven fabric having a three-dimensional structure in which fibers have been bound together in advance; then forming nonwoven fabric fragments by pulverizing the nonwoven fabric; and mixing the nonwoven fabric fragments with hydrophilic fibers. Patent Literature 1 describes employing a cutter mill system as a means for pulverizing the nonwoven fabric, and forming nonwoven fabric fragments having an average dimension of 3 to 25 mm.

CITATION LIST

Patent Literature

Patent Literature 1: JP 2002-301105A

SUMMARY OF INVENTION

The present invention is a method for manufacturing an absorbent member including synthetic fibers. The manufacturing method involves: a transporting step of transporting a plurality of sheet fragments including synthetic fibers to an accumulating portion by using a transporting portion; an accumulating step of accumulating, in the accumulating portion, the plurality of sheet fragments transported in the transporting step, and forming an accumulation which is a constituent member of the absorbent member; and a pressing step of pressing the accumulation over its entirety in a thickness direction.

DESCRIPTION OF EMBODIMENTS

When an absorbent member is manufactured by using nonwoven fabric fragments having a certain degree of size, like the absorbent member disclosed in Patent Literature 1, large gaps are likely to be created among adjacent nonwoven fabric fragments, and, depending on the size of the gaps, spreading of body fluid may be inhibited. This may result in deterioration in absorbency when the absorbent member absorbs body fluid.

The present invention relates to providing a method for manufacturing an absorbent member having excellent absorbency.

The present invention is described below according to preferred embodiments thereof with reference to the drawings. The manufacturing method of the present invention is a method for manufacturing an absorbent member including sheet fragments including synthetic fibers. The absorbent member manufactured according to the present invention can suitably be used as an absorbent member for an absorbent article. An absorbent article is used for absorbing and retaining body fluid excreted from the body, with examples mainly including urine and menstrual blood. Examples of absorbent articles include disposable diapers, sanitary napkins, incontinence pads, and pantiliners, but are not limited thereto, and widely encompass articles used for absorbing liquids discharged from the human body. Typically, an absorbent article includes a liquid-permeable topsheet, a liquid-impermeable or water-repellent backsheet, and a liquid-retentive absorbent member interposed between the two sheets. The absorbent member is the absorbent member formed by the absorbent member manufacturing method of the present invention.

Figure 1:
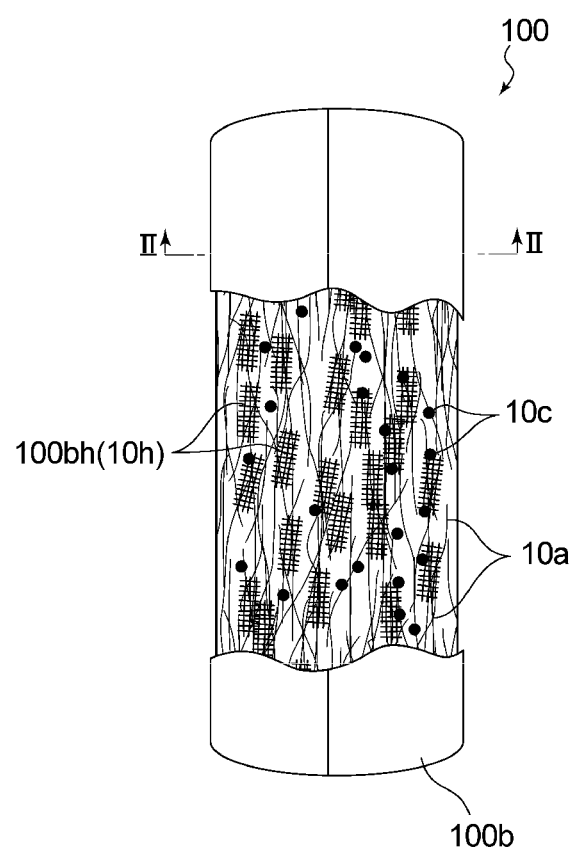
FIG. 1 is a plan view illustrating a preferred embodiment of an absorbent member, with a portion of a core-wrap sheet cut away, manufactured by an absorbent member manufacturing method of the invention.
Figure 2:
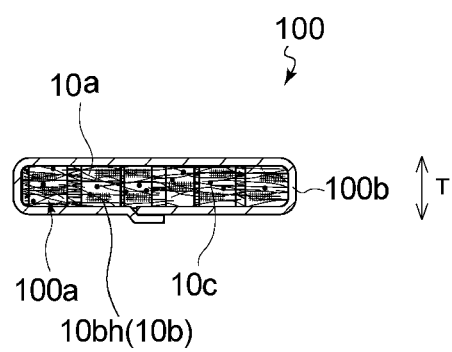
FIG. 2 is a cross-sectional view taken along line II-II of the absorbent member illustrated in FIG. 1.
Figure 3:
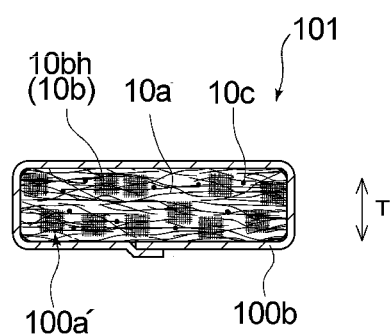
FIG. 3 is a cross-sectional view of a portion corresponding to the cross-sectional view taken along line II-II, before pressing the absorbent member illustrated in FIG. 1.

FIG. 1 is a plan view illustrating an embodiment of an absorbent member 100, with a portion of a core-wrap sheet 100*b* cut away, manufactured by an absorbent member manufacturing method of the present embodiment. FIG. 2 illustrates a cross-sectional view taken along line II-II of the absorbent member 100 illustrated in FIG. 1. FIG. 3 illustrates a cross-sectional view of an absorbent member precursor 101 before being pressed in the thickness direction. The absorbent member 100 includes a plurality of sheet fragments 10*bh* including synthetic fibers 10*b* (simply referred to hereinafter also as "sheet fragments 10*bh*"); in the present embodiment, as illustrated in FIGS. 1 and 2, the absorbent member 100 includes an accumulation 100*a* including not only the sheet fragments 10*bh* but also hydrophilic fibers 10*a* and absorbent particles 10*c*. The absorbent member 100 may be a single layer or multi-layers including two or more layers, so long as it includes the sheet fragments 10*bh*. In the present embodiment, the absorbent member 100 includes a single-layer accumulation 100*a* in which the hydrophilic fibers 10a, the sheet fragments 10bh, and the absorbent particles 10c are dispersed uniformly. The accumulation 100a is a constituent member of the absorbent member 100, and the absorbent member 100 is formed by covering the accumulation 100a with a core-wrap sheet 100b. The absorbent member 100 has a shape that is long in the longitudinal direction, which corresponds to the front-rear direction of a wearer when the absorbent article is worn.

The absorbent member 100 illustrated in FIG. 2 is formed by pressing the absorbent member precursor 101 illustrated in FIG. 3. The precursor 101 is formed by covering, with a core-wrap sheet 100b, an accumulation 100a' before being pressed. The accumulation 100a' includes regions respectively having different quantities of the sheet fragments 10bh overlapping one another over an entire region in the thickness direction T, and such regions are present in a dispersed manner in the longitudinal direction, which is one direction of the accumulation 100a', and the lateral direction which is orthogonal to the longitudinal direction. Thus, in the accumulation 100a', regions respectively having different densities of presence of sheet fragments 10bh are present in a dispersed manner in both the longitudinal direction and the lateral direction. By pressing, in the thickness direction, the precursor 101 including this accumulation 100a' before being pressed, the accumulation 100a illustrated in FIG. 2 is provided with a sparse-dense structure in which there is a distribution in density of presence of the hydrophilic fibers 10a in both the longitudinal direction and the lateral direction, as illustrated in FIG. 1. Herein, the density of presence of the sheet fragments 10bh refers to the number of sheet fragments 10bh that are present per 1 mm² in a discretionary cross section that is parallel to the thickness direction of the accumulation 100a. The density of presence of the hydrophilic fibers 10a refers to the number of hydrophilic fibers 10a that are present per 1 mm² in a discretionary cross section that is parallel to the thickness direction of the accumulation 100a.

For example, the following method may be employed for the method for measuring the density of presence of the hydrophilic fibers 10a.

An absorbent member 100 is cut in the thickness direction Z by using a Feather razor blade (product number FAS-10 from Feather Safety Razor Co., Ltd.). The cut surface of the absorbent member 100 is magnified and observed with a scanning electron microscope (adjusted to a magnification capable of counting around 30 to 60 fiber cross sections; from 150× to 500×), and the number of cross sections of fibers cut by the cut surface per a given area (around 0.5 mm²) is counted. The measurement is performed at three sites along the thickness direction, and the average is found as the density of presence of the hydrophilic fibers 10a at that position. The scanning electron microscope employed is JCM-5100 (product name) from JEOL Ltd.

The accumulation 100a illustrated in FIG. 2 has gaps that are smaller than the gaps among the sheet fragments 10bh in the accumulation 100a' illustrated in FIG. 3, and the small gaps are arranged substantially uniformly among the sheet fragments 10bh, to create a closely packed sparse-dense structure. In this sparse-dense structure, regions in which the number of sheet fragments 10bh is relatively large and the number of hydrophilic fibers 10a is small constitute sparse regions, whereas regions in which the number of sheet fragments 10bh is relatively small and the number of hydrophilic fibers 10a is large constitute dense regions. By providing the accumulation 100a with the aforementioned closely packed sparse-dense structure, diffusion and absorption of liquid can be performed efficiently, and the absorbency of the absorbent member 100 can be improved.

The accumulation 100a includes a plurality of the sheet fragments 10bh. Each sheet fragment 10bh has a substantially rectangular shape. The average length of the sheet fragments 10bh is preferably from 0.3 to 30 mm, more preferably from 1 to 15 mm, even more preferably from 2 to 10 mm. Herein, in cases where each sheet fragment 10bh is a rectangle, the average length refers to the average value of the length of a side in the longitudinal direction. In cases where each sheet fragment 10bh is a square, the average length refers to the average value of the length of any one of the four sides. When the average length of the sheet fragments 10bh is 0.3 mm or greater, a sparse structure can easily be formed in the absorbent member 100. When the average length is 30 mm or less, the absorbent member 100 is less likely to cause an unnatural feel to the wearer, and absorbency is less likely to become uneven depending on the positions within the absorbent member 100. The average width of the sheet fragments 10bh is preferably from 0.1 to 10 mm, more preferably from 0.3 to 6 mm, even more preferably from 0.5 to 5 mm. Herein, in cases where each sheet fragment 10bh is a rectangle, the average width refers to the average value of the length of a side in the lateral direction. In cases where each sheet fragment 10bh is a square, the average width refers to the average value of the length of any one of the four sides. When the average width of the sheet fragments 10bh is 0.1 mm or greater, a sparse structure can easily be formed in the absorbent member 100. When the average width is 10 mm or less, the absorbent member 100 is less likely to cause an unnatural feel to the wearer, and absorbency is less likely to become uneven depending on the positions within the absorbent member 100.

For the fiber materials forming the absorbent member 100, various materials conventionally used in absorbent members for absorbent articles can be used without particular limitation. Examples of the hydrophilic fibers 10a include pulp fibers, rayon fibers, and cotton fibers. Examples of the synthetic fibers 10b include short fibers made of polyethylene, polypropylene, or polyethylene terephthalate. The sheet fragments 10bh are not particularly limited so long as they are in a sheet form, but are preferably a nonwoven fabric. Further, materials constituting the absorbent member 100 not only include the hydrophilic fibers 10a and the synthetic fibers 10b, but also include absorbent particles 10c. Examples of the absorbent particles 10c include starch-based, cellulose-based, synthetic polymer-based, and superabsorbent polymer-based particles. Examples of superabsorbent polymers that may be used include starch-acrylic acid (acrylate) graft copolymers, saponified products of starch-acrylonitrile copolymers, crosslinked products of sodium carboxymethyl cellulose, and acrylic acid (acrylate) polymers. For constituent members constituting the absorbent member 100, it is also possible to use, for example, deodorants and antibacterial agents as necessary. Examples of the core-wrap sheet 100b include tissue paper and liquid-permeable nonwoven fabrics.

Figure 4:
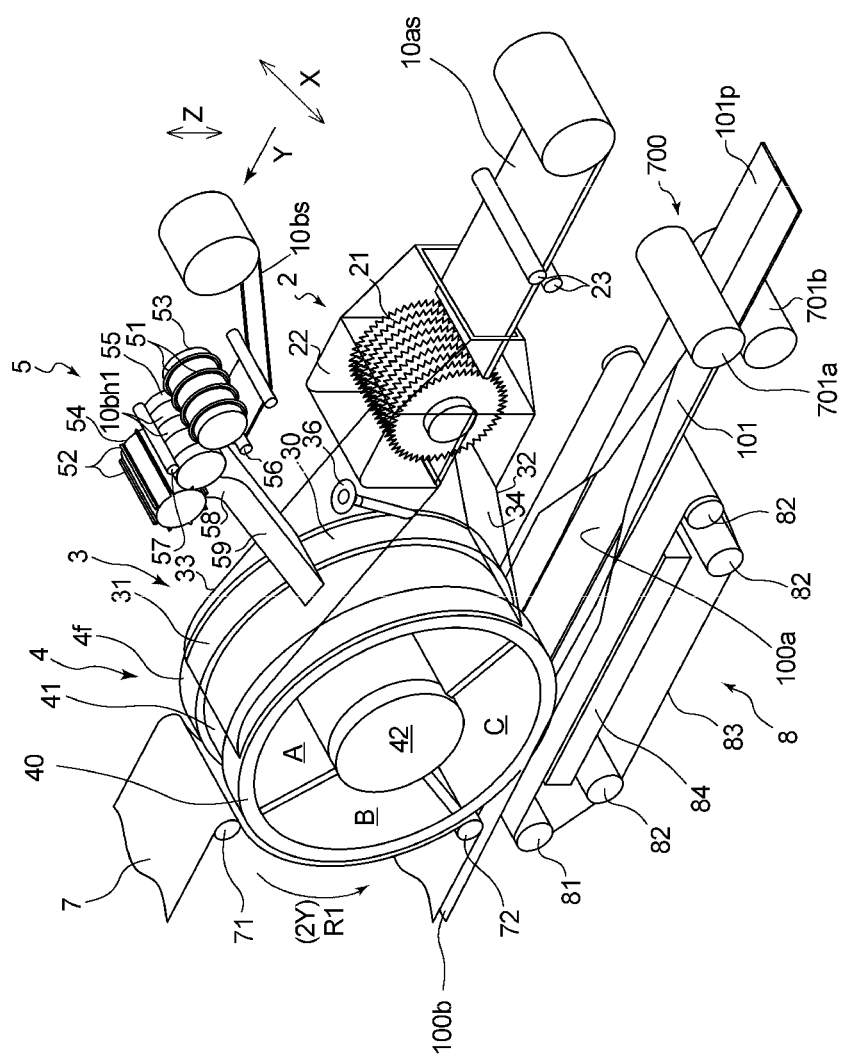
FIG. 4 is a schematic perspective view illustrating a preferred embodiment of a manufacturing device for manufacturing the absorbent member illustrated in FIG. 1.
Figure 5:
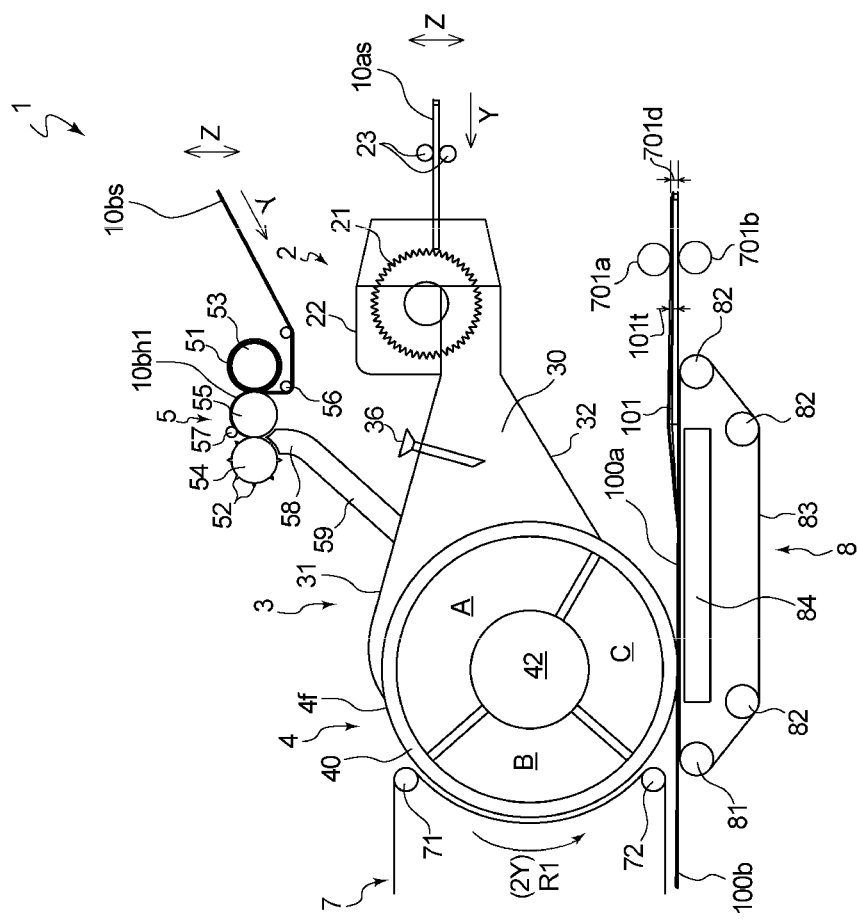
FIG. 5 is a schematic side view illustrating the manufacturing device illustrated in FIG. 4 as viewed from a lateral side.

Next, the absorbent member manufacturing method of the present invention is described with reference to FIGS. 4 to 6, taking, as an example, a method for manufacturing the aforementioned absorbent member 100. FIGS. 4 and 5 illustrate an overall configuration of a manufacturing device 1 used for performing the present manufacturing method.

On describing the method for manufacturing the absorbent member 100, first, the manufacturing device 1 will be described.

The material of the accumulation 100a only needs to include at least the sheet fragments 10bh, but the aforementioned absorbent member 100 includes the hydrophilic fibers 10a and the absorbent particles 10c in addition to the sheet fragments 10bh. As illustrated in FIGS. 4 and 5, the manufacturing device 1 for manufacturing the absorbent member 100 includes at least: a duct 3 that transports the material of the absorbent member 100; an accumulating depression 41, which is an example of an accumulating portion that is arranged on the downstream side in the transporting direction within the duct 3 and in which the material of the absorbent member 100 is accumulated; a supplying portion 5 that supplies the sheet fragments 10bh to inside the duct 3; and a pressing portion 700 that presses the accumulation 100a' accumulated in the accumulating depression 41. More specifically, the manufacturing device 1 includes, from the upstream side toward the downstream side in the transporting direction: a defibrating portion 2 that defibrates a hydrophilic sheet 10as including the hydrophilic fibers 10a by using a defibrating machine 21; a duct 3 that transports the material of the absorbent member 100 by carrying it on an airflow; a supplying portion 5 that supplies the synthetic fibers 10b to inside the duct 3 in midstream of the duct 3; a rotary drum 4 arranged downstream of the duct 3 adjacent thereto; a press-down belt 7 arranged along the rotary drum 4's outer circumferential surface 4f located on the opposite side from the duct 3; a vacuum conveyor 8 arranged below the rotary drum 4; and a pressing portion 700 arranged downstream of the vacuum conveyor. The accumulating depression 41 is provided in the outer circumferential surface of the rotary drum 4.

In the description below, the direction in which a continuous fiber sheet 10bs including the synthetic fibers 10b is transported is described as the Y direction, the width direction of the fiber sheet 10bs being transported and the direction orthogonal to the transporting direction are the X direction, and the thickness direction of the fiber sheet 10bs being transported is the Z direction.

Further, the later-described first direction is the direction extending in the transporting direction Y, and refers to a direction wherein the angle formed between it and the transporting direction Y is within a range of less than 45 degrees. In the present embodiment, the first direction matches the direction parallel to the transporting direction Y.

Further, the later-described second direction is a direction intersecting with the first direction. In the present embodiment, the second direction is a direction orthogonal to the first direction, and matches the direction parallel to the width direction X of the fiber sheet 10bs and the absorbent member 100 being transported.

As illustrated in FIGS. 4 and 5, the manufacturing device 1 includes a defibrating portion 2 that defibrates a continuous hydrophilic sheet 10as including the hydrophilic fibers 10a. The defibrating portion 2 includes: a defibrating machine 21 that defibrates the hydrophilic sheet 10as; and a casing 22 that covers the upper side of the defibrating machine 21. The defibrating portion 2 is a section that supplies, to inside the duct 3, the defibrated hydrophilic fibers 10a which are a material of the absorbent member 100. The defibrating portion 2 also includes a pair of feed rollers 23, 23 that supplies the hydrophilic sheet 10as to the defibrating machine 21.

Of the pair of feed rollers 23, 23, at least one roller is structured so as to be rotated by a driving device (not illustrated). The feed rollers 23, 23 are nipping-type rollers. An example of the driving device is a servomotor. From the viewpoint of preventing slipping of the hydrophilic sheet 10as, it is preferable that both of the feed rollers 23, 23 are rotated by the driving device. In this case, the pair of feed rollers 23, 23 may be driven directly by the driving device, or one of the rollers may be driven by the driving device and the drive may be transmitted to the other roller by a transmission means such as a gear. From the viewpoint of further preventing slipping of the hydrophilic sheet 10as, the pair of feed rollers 23, 23 may be made less slippery by forming, in the surface thereof, grooves extending in the axial direction over the entire circumference. In addition to the pair of feed rollers 23, 23, other rollers for assisting the transportation of the hydrophilic sheet 10as may be provided.

As illustrated in FIGS. 4 and 5, the manufacturing device 1 includes a duct 3 serving as a transporting portion that transports the material of the accumulation 100a. The duct 3 extends from the defibrating portion 2 up to the rotary drum 4, and the duct 3's opening on the downstream side covers the outer circumferential surface 4f which is located at the rotary drum 4's space A which is maintained at a negative pressure. The duct 3 includes a top plate 31 forming the top surface, a bottom plate 32 forming the bottom surface, and side walls 33, 34 forming the respective side surfaces. By activating an air suction fan (not illustrated) of the rotary drum 4, an airflow for carrying the material of the absorbent member 100 toward the outer circumferential surface 4f of the rotary drum 4 is created inside the space surrounded by the top plate 31, the bottom plate 32, and the side walls 33, 34 of the duct 3. Stated differently, the inside of the duct 3 serves as a flow path 30.

Further, as illustrated in FIGS. 4 and 5, the manufacturing device 1 manufacturing the absorbent member 100 including the absorbent particles 10c has an absorbent particle dispersing tube 36 that supplies absorbent particles 10c to inside the duct 3, the absorbent particle dispersing tube being arranged at the top plate 31 of the duct 3. The absorbent particle dispersing tube 36 is configured such that the absorbent particles 10c are discharged, by a device such as a screw feeder (not illustrated), from a dispersing opening provided at the tip end of the absorbent particle dispersing tube 36, and are supplied to inside the duct 3. Further, the supply amount of the absorbent particles 10c to the absorbent particle dispersing tube 36 can be adjusted by the device such as a screw feeder. Thus, by adjusting the supply amount of the absorbent particles 10c to the absorbent particle dispersing tube 36 by a device such as a screw feeder, the amount of absorbent particles 10c dispersed to the flow path 30 can be adjusted freely, and as a result, the blending ratio of the absorbent particles 10c in the hydrophilic fibers 10a and the synthetic fibers 10b can be adjusted freely. The absorbent particle dispersing tube 36 is arranged between the defibrating portion 2 and the supplying portion 5 for the synthetic fibers 10b. By changing the arrangement position of the absorbent particle dispersing tube 36, the distribution of the absorbent particles 10c in the accumulation 100a can be adjusted. Further, by changing the height of the dispersing opening of the absorbent particle dispersing tube 36 (i.e., the distance between the top plate 31 and the dispersing opening of the absorbent particle dispersing tube 36), the distribution of the absorbent particles 10c in the thickness direction (Z direction) of the accumulation 100a can be adjusted.

As illustrated in FIGS. 4 and 5, the manufacturing device 1 includes a rotary drum 4. The rotary drum 4 has, in its outer circumferential surface 4f, an accumulating depression 41 which serves as an accumulating portion for accumulating the material of the absorbent member to form an accumulation 100a'. The rotary drum 4 is cylindrical, and, by receiving motive power from a prime mover (not illustrated) such as a motor, a member 40 forming the outer circumferential surface 4f rotates in the direction of arrow R1 about a horizontal axis. The rotary drum 4 includes: a member 40 forming the outer circumferential surface 4f; and a drum body 42 located more inward than the member 40. The drum body 42 is fixed and does not rotate. The accumulating depression 41 of the rotary drum 4 is formed in the member 40 forming the outer circumferential surface 4f, and is arranged continuously over the entire circumference in the circumferential direction (2Y direction) of the rotary drum 4. In the figure, 2Y indicates the circumferential direction of the rotary drum 4, and X indicates the width direction of the rotary drum 4 (i.e., direction parallel to the rotation axis of the rotary drum 4). As described above, the accumulating depression 41 in this manufacturing device 1 is arranged continuously over the entire circumference in the circumferential direction 2Y of the rotary drum 4, but may be configured so that a plurality of accumulating depressions are arranged at predetermined intervals in the circumferential direction 2Y of the rotary drum 4.

As illustrated in FIGS. 4 and 5, the drum body 42 of the rotary drum 4 has therein a plurality of spaces which are independent from one another, and there are three spaces A to C, for example. The spaces A to C are partitioned off from one another by plates provided from the rotation axis side of the rotary drum 4 toward the outer circumferential surface 4f side. The rotary drum 4 is connected to an air suction fan (not illustrated) serving as an air suction mechanism. By driving the air suction fan, the pressure in the respective spaces partitioned off inside the rotary drum 4 can be adjusted. In the manufacturing device 1, the suction force in the region corresponding to the space A, which is the upstream region located in a region where the outer circumferential surface 4f is covered by the duct 3, can be made stronger or weaker than the suction force in the regions corresponding to the spaces B and C, which are downstream regions, and the space A is maintained at a negative pressure. Note, however, that the manner in which the spaces inside the drum body 42 are partitioned is not limited to the aforementioned configuration. For example, the drum body 42's space A which is maintained at a negative pressure may further be partitioned off into a plurality of spaces, and the pressure in each of the further-partitioned spaces may be adjusted. Further, for example, the drum body 42's space B may further be partitioned off into a plurality of spaces, and the pressure in each of the further-partitioned spaces may be adjusted; further, the pressure in the space located closest to the space A may be adjusted to match the pressure of the space A, so that a negative pressure region can be formed up to a point slightly ahead of where the accumulating depression 41 exits the duct 3.

The bottom surface of the accumulating depression 41 is constituted by a porous member (not illustrated), and, while the accumulating depression 41 in the outer circumferential surface 4f passes over the space in the rotary drum 4 that is maintained at a negative pressure, the porous member functions as suction holes for sucking the material of the absorbent member 100.

As illustrated in FIGS. 4 and 5, the manufacturing device 1 includes a supplying portion 5 that supplies the sheet fragments 10bh to inside the duct 3. The supplying portion 5 includes cutter blades 51, 52 that cut a fiber sheet 10bs at predetermined lengths in the first direction (Y direction) and the second direction (X direction), and form the sheet fragments 10bh. The supplying portion 5 includes a first cutter roller 53 including a plurality of cutter blades 51 that cut in the first direction, and a second cutter roller 54 including a plurality of cutter blades 52 that cut in the second direction. The supplying portion 5 includes a single receiving roller 55 arranged in opposition to the first cutter roller 53 and the second cutter roller 54.

Figure 6:
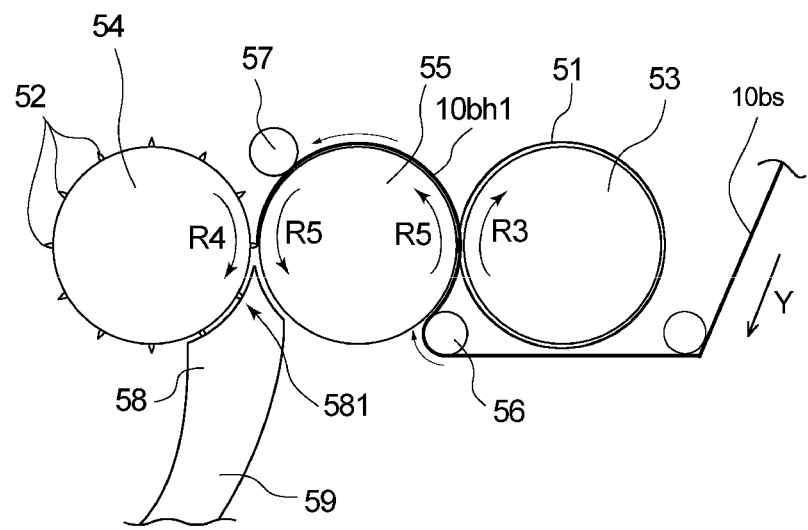
FIG. 6 is an enlarged side view illustrating a supplying portion of the manufacturing device illustrated in FIG. 4.

As illustrated in FIGS. 4 to 6, the surface of the first cutter roller 53 is provided with a plurality of cutter blades 51, 51, 51, . . . extending continuously over the entire outer circumference of the first cutter roller 53 along the circumferential direction of the first cutter roller 53, the cutter blades being lined up in the axial direction (X direction) of the first cutter roller 53. By receiving motive power from a prime mover such as a motor, the first cutter roller 53 rotates in the direction of arrow R3. The interval between the cutter blades 51, 51, 51, . . . adjacent to one another in the axial direction of the first cutter roller 53 substantially corresponds to the width (length in the lateral direction; length in the X direction) of each sheet fragment 10bh formed by cutting. Strictly speaking, depending on the tension during sheet transportation, the fiber sheet 10bs may be cut in a state where it is shrunken in the width direction X; thus, by releasing this tension, the width of each produced sheet fragment 10bh may become wider than the interval between the cutter blades 51, 51, 51, . . . .

As illustrated in FIGS. 4 to 6, the surface of the second cutter roller 54 is provided with a plurality of cutter blades 52, 52, 52, . . . extending continuously over the entire width of the second cutter roller 54 along the axial direction of the second cutter roller 54, the cutter blades being arranged with intervals therebetween in the circumferential direction of the second cutter roller 54. By receiving motive power from a prime mover such as a motor, the second cutter roller 54 rotates in the direction of arrow R4.

As illustrated in FIGS. 4 to 6, the receiving roller 55 is a flat roller having a flat surface. By receiving motive power from a prime mover such as a motor, the receiving roller 55 rotates in the direction of arrow R5.

As illustrated in FIGS. 4 to 6, opposing the surface of the receiving roller 55, the supplying portion 5 includes, in order from the upstream side toward the downstream side in the rotating direction (the direction of arrow R5): a free roller 56 that supplies the fiber sheet 10bs between the receiving roller 55 and the first cutter roller 53; the first cutter roller 53 that cuts the fiber sheet 10bs in the first direction; a nip roller 57 that supplies, between the receiving roller 55 and the second cutter roller 54, a plurality of continuous sheet fragments 10bh1 that have been cut in the first direction and extend in the first direction; and the second cutter roller 54 that cuts the sheet fragment strips 10bh1 in the second direction. The supplying portion 5 also includes a feed roller (not illustrated) that transports the fiber sheet 10bs, and the feed roller supplies the fiber sheet 10bs between the receiving roller 55 and the first cutter roller 53. The feed roller is configured so as to be rotated by a driving device such as a servomotor. From the viewpoint of preventing the fiber sheet 10bs from slipping, the feed roller may be made less slippery by forming, in the surface thereof, grooves extending in the axial direction over the entire circumference, or by subjecting the entire circumference to a coating treatment for increasing friction force. Further, slipping can be suppressed by sandwiching the fiber sheet between the feed roller and a nip roller.

As illustrated in FIGS. 4 to 6, the supplying portion 5 includes a suction nozzle 58 that sucks the sheet fragments 10*bh* formed by the second cutter roller 54. The suction nozzle 58 has a suction opening 581 that is arranged below the second cutter roller 54—i.e., more toward the downstream side, in the second cutter roller 54's rotating direction (the direction of arrow R4), than the closest point between the second cutter roller 54 and the receiving roller 55. The suction opening 581 of the suction nozzle 58 extends over the entire width of the second cutter roller 54. From the viewpoint of improving the ability to suck the sheet fragments 10*bh*, it is preferable that the suction opening 581 of the suction nozzle 58 is arranged below the receiving roller 55 and the second cutter roller 54 so as to be in opposition between the receiving roller 55 and the second cutter roller 54. From the viewpoint of further improving the ability to suck the sheet fragments 10*bh*, it is preferable that the suction opening 581 of the suction nozzle 58 covers the outer surface of the second cutter roller 54 such that, as viewed from the side surface of the receiving roller 55 and the second cutter roller 54, the length of an arc of the suction opening 581 opposing the second cutter roller 54 is longer than the length of an arc of the suction opening 581 opposing the receiving roller 55, as illustrated in FIG. 6.

As illustrated in FIGS. 4 and 5, the suction nozzle 58 is connected by a suction tube 59 to the top plate 31 side of the duct 3. The sheet fragments 10*bh* sucked from the suction opening 581 of the suction nozzle 58 are supplied to inside the duct 3 in midstream of the duct 3 through the suction tube 59. The connecting position of the suction tube 59 and the duct 3 is located between the defibrating portion 2 side and the rotary drum 4 side in the duct 3, and is located more toward the downstream side, in the duct 3, than the absorbent particle dispersing tube 36. The connecting position of the suction tube 59 and the duct 3 is, however, not limited thereto, and for example, it may be on the bottom plate 32 side and not the top plate 31 side of the duct 3.

As illustrated in FIGS. 4 and 5, the press-down belt 7 is arranged adjacent to the position of the duct 3 on the downstream side thereof, and is arranged along the outer circumferential surface 4*f* located at space B of the rotary drum 4. The space B is set to zero pressure (atmospheric pressure) or to a negative pressure weaker than that of the space A of the rotary drum 4. The press-down belt 7 is an endless, air-permeable or air-impermeable belt, bridges rollers 71 and 72, and rotates so as to follow the rotation of the rotary drum 4. Thanks to the press-down belt 7, the accumulation 100*a* in the accumulating depression 41 can be retained inside the accumulating depression 41 until the accumulation is transferred onto the vacuum conveyor 8.

As illustrated in FIGS. 4 and 5, the vacuum conveyor 8 is arranged below the rotary drum 4, and is arranged at the outer circumferential surface 4*f* located in the rotary drum 4's space C in which the pressure is set to zero (atmospheric pressure) or to a slightly positive pressure. A weak positive pressure can be achieved by, for example, blowing air from the inside of the drum body 42 toward outside the outer circumferential surface 4*f*. The vacuum conveyor 8 includes: an endless air-permeable belt 83 that bridges a drive roller 81 and driven rollers 82, 82; and a vacuum box 84 arranged in a position opposing the outer circumferential surface 4*f* located at the space C of the rotary drum 4 across the air-permeable belt 83. A core-wrap sheet 100*b*, which is made of tissue paper or a liquid-permeable nonwoven fabric, is introduced onto the vacuum conveyor 8.

On the downstream side of the vacuum conveyor 8, the manufacturing device 1 further includes folding guide plates (not illustrated) which fold the core-wrap sheet 100*b* in the width direction so as to cover the accumulation 100*a*' placed on one surface of the core-wrap sheet 100*b*. The folding guide plates (not illustrated) fold, onto the accumulation 100*a*', both lateral sides of the core-wrap sheet 100*b* which extend along the transporting direction, to form an absorbent member precursor 101.

As illustrated in FIGS. 4 and 5, the pressing portion 700 is arranged downstream of the folding guide plates (not illustrated). The pressing portion 700 includes a pair of metal flat rollers 701*a*, 701*b* having a flat surface. At least one of the rollers is configured so as to be rotated by a driving device (not illustrated). The driving device may be a servomotor, for example. From the viewpoint of pressing the entire precursor 101 formed by using the folding guide plates (not illustrated), it is preferable that both of the flat rollers 701*a*, 701*b* are rotated by the driving device. In this case, the pair of flat rollers 701*a*, 701*b* may be driven directly by the driving device, or one of the rollers may be driven by the driving device and the drive may be transmitted to the other roller by a transmission means such as a gear. Further, the pair of flat rollers 701*a*, 701*b* is configured such that the distance between the rollers is adjustable by moving one flat roller 701*a* in a direction separating from the other flat roller 701*b* by using a distance adjusting device (not illustrated). The distance adjusting device may be a distance adjusting device employing a ball screw, for example.

Further, the manufacturing device 1 also includes a cutting device (not illustrated) on the downstream side of the pressing portion 700. The cutting device manufactures separate absorbent members 100. For the cutting device, it is possible to use, without particular limitation, any type of device conventionally used for cutting a continuous strip of absorbent members in manufacturing absorbent articles, such as sanitary napkins, light incontinence pads, pantiliners, and diapers. An example of the cutting device is a pair of a cutter roller having a cutting blade on its circumferential surface and an anvil roller having a flat and smooth circumferential surface for receiving the cutting blade.

Next, a method for manufacturing an absorbent member 100 by using the aforementioned manufacturing device 1—i.e., an embodiment of the absorbent member manufacturing method of the present invention—will be described.

As illustrated in FIGS. 4 and 5, the method for manufacturing an absorbent member 100 involves: a transporting step of transporting a plurality of sheet fragments 10*bh* to the accumulating depression 41, which serves as an accumulating portion, by using the duct 3, which serves as a transporting portion; an accumulating step of accumulating, in the accumulating depression 41, the plurality of sheet fragments 10*bh* transported in the transporting step, and forming an accumulation 100*a*' which is a constituent member of the absorbent member 100; and a pressing step of pressing the formed accumulation 100*a*' over its entirety in the thickness direction. Further, the method for manufacturing an absorbent member 100 according to the present embodiment involves a defibrating step of defibrating a continuous hydrophilic sheet 10*as* and obtaining hydrophilic fibers 10*a*. Further, the method for manufacturing an absorbent member 100 according to the present embodiment involves: a cutting step of cutting a fiber sheet 10*bs* at predetermined lengths in the first direction and the second direction, and forming the sheet fragments 10*bh*; and a suction step of sucking the sheet fragments 10*bh* obtained in the cutting step and supplying them to inside the duct 3 serving as the transporting portion. Further, the method for manufacturing an absorbent member 100 according to the present embodiment involves a covering step of covering the formed accumulation 100a' with a core-wrap sheet 100b, to thereby form a precursor 101, and in the pressing step, the precursor 101 formed in the covering step is pressed over its entirety in the thickness direction. The method for manufacturing an absorbent member 100 will be described in detail below.

First, the space A inside the rotary drum 4 and the inside of the vacuum box 84 for the vacuum conveyor 8 are set to a negative pressure by activating air suction fans (not illustrated) respectively connected thereto. By creating a negative pressure inside the space A, an airflow for transporting the material of the absorbent member 100 to the outer circumferential surface 4f of the rotary drum 4 is created inside the duct 3. Further, the defibrating machine 21 and the rotary drum 4 are rotated, the first cutter roller 53, the second cutter roller 54 and the receiving roller 55 are rotated, and the press-down belt 7 and the vacuum conveyor 8 are activated.

Next, as illustrated in FIGS. 4 and 5, the defibrating step is performed for defibrating a continuous hydrophilic sheet 10as by supplying the sheet to the defibrating machine 21 by using the pair of feed rollers 23, 23, and obtaining hydrophilic fibers 10a. The hydrophilic fibers 10a, which are a defibrated fiber material, are supplied from the defibrating machine 21 to the duct 3. The pair of feed rollers 23, 23 controls the speed for supplying the hydrophilic sheet 10as to the defibrating machine 21; in the defibrating step, the supplying of the hydrophilic sheet 10as to the defibrating machine 21 is controlled.

This method for manufacturing an absorbent member 100 further includes a cutting step separately from the defibrating step. In the cutting step, as illustrated in FIG. 6, the fiber sheet 10bs is cut and the sheet fragments 10bh are formed by using: the first cutter roller 53 including the cutter blades 51 that cut in the first direction (Y direction); and the second cutter roller 54 including the cutter blades 52 that cut in the second direction (X direction). In the cutting step, by using the first cutter roller 53 which cuts the fiber sheet 10bs in the first direction, the second cutter roller 54 which cuts the sheet in the second direction, and a single receiving roller 55 arranged in opposition to the first cutter roller 53 and the second cutter roller 54: the fiber sheet 10bs is introduced between the first cutter roller 53 and the receiving roller 55 and is cut at a predetermined length in the first direction to form sheet fragment strips 10bh1; and the formed sheet fragment strips 10bh1 are transported by the receiving roller 55 and are cut at a predetermined length in the second direction between the second cutter roller 54 and the receiving roller 55 to form the sheet fragments 10bh. The cutting step of the present embodiment is described in detail below.

In the cutting step, as illustrated in FIG. 6, the fiber sheet 10bs is transported by using the feed roller (not illustrated). The feed roller controls the speed for transporting the fiber sheet 10bs; in the cutting step, the transportation speed of the fiber sheet 10bs is controlled.

As illustrated in FIG. 6, in the cutting step, the fiber sheet 10bs transported by the feed roller is introduced, by the free roller 56, between the receiving roller 55 and the first cutter roller 53. The fiber sheet 10bs is introduced between the receiving roller 55, which is a flat roller rotating in the direction of arrow R5, and the first cutter roller 53, which rotates in the direction of arrow R3, and, with the plurality of cutter blades 51, 51, 51, . . . that are provided on the surface of the first cutter roller 53 and extend along the first direction with intervals therebetween in the second direction, the fiber sheet 10bs is cut in the first direction at positions with intervals therebetween in the second direction. Performing cutting as described above forms a plurality of sheet fragment strips 10bh1 which extend in the first direction and are arranged side by side in the second direction. The plurality of cutter blades 51, 51, 51, . . . are arranged on the surface of the first cutter roller 53 at even intervals in the second direction. Thus, the fiber sheet 10bs is cut at even intervals, and a plurality of sheet fragment strips 10bh1 having the same width (length in the second direction) are formed. From the viewpoint of ensuring that the sheet fragments 10bh have the necessary dimensions to achieve predetermined effects, it is preferable that the average width of the sheet fragment strips 10bh1 formed in the cutting step is from 0.1 to 10 mm, more preferably from 0.3 to 6 mm, even more preferably from 0.5 to 5 mm. In the present embodiment, the width of each sheet fragment strip 10bh1 cut by the first cutter roller 53 matches the length of the side, in the lateral direction, of each sheet fragment 10bh ultimately formed. Cutting, however, may be performed such that the width of each sheet fragment strip 10bh1 cut by the first cutter roller 53 corresponds to the length of the side, in the length direction, of each sheet fragment 10bh ultimately formed. In this case, the average width of the sheet fragment strips 10bh1 cut by the first cutter roller 53 is preferably from 0.3 to 30 mm, more preferably from 1 to 15 mm, even more preferably from 2 to 10 mm. The plurality of sheet fragment strips 10bh1 that have been formed are transported on the circumferential surface of the receiving roller 55 which rotates in the direction of arrow R5, are transported between the receiving roller 55 and the nip roller 57, and are introduced between the receiving roller 55 and the second cutter roller 54 by the nip roller 57.

Then, as illustrated in FIG. 6, in the cutting step, the plurality of sheet fragment strips 10bh1, which are arranged side by side in the second direction and extend in the first direction, are introduced between the receiving roller 55, which rotates in the direction of arrow R5, and the second cutter roller 54, which rotates in the direction of arrow R4, and, with the plurality of cutter blades 52, 52, 52, . . . that are provided on the surface of the second cutter roller 54 and extend over the entire width of the roller along the second direction with even intervals therebetween in the rotating direction of the second cutter roller 54, the plurality of sheet fragment strips 10bh1 are cut along the second direction and intermittently in the first direction. Performing cutting as described above forms a plurality of rectangular sheet fragments 10bh in which the length in the first direction is longer than the length in the second direction. The plurality of cutter blades 52, 52, 52, . . . are arranged on the surface of the second cutter roller 54 at even intervals in the circumferential direction thereof. Thus, the plurality of sheet fragment strips 10bh1 are cut at even intervals, and a plurality of rectangular sheet fragments 10bh having the same length in the first direction are formed. From the viewpoint of ensuring that the sheet fragments 10bh have the necessary dimensions to achieve predetermined effects, it is preferable that the average length of each sheet fragment 10bh formed in the cutting step is from 0.3 to 30 mm, more preferably from 1 to 15 mm, even more preferably from 2 to 10 mm. In the present embodiment, the length of each sheet fragment 10bh cut by the second cutter roller 54 matches the length of the side, in the length direction, of each sheet fragment 10bh. Cutting, however, may be performed such that the length of each sheet fragment 10bh cut by the second cutter roller 54 corresponds to the length of the side, in the lateral direction, of each sheet fragment 10bh. In this case, the length (width) of each sheet fragment 10bh cut by the second cutter roller 54 is preferably from 0.1 to 10 mm, more preferably from 0.3 to 6 mm, even more preferably from 0.5 to 5 mm.

In the cutting step, the fiber sheet 10bs is cut in the first direction and cut at a predetermined length in the second direction to thereby obtain the sheet fragments 10bh. Thus, the size of the obtained sheet fragments 10bh can easily be adjusted to an intended size, and a large amount of sheet fragments 10bh with the same size can easily be manufactured with high precision. It should be noted that, even in cases where the sheet fragments 10bh are formed by cutting in the first direction or the second direction by using the first cutter roller 53 including the cutter blades 51 or the second cutter roller 54 including the cutter blades 52, the cutting may make the synthetic fibers fuzzy at the periphery of the formed sheet fragments 10bh. Further, if the cutter blades 51, 52 become worn out or otherwise deteriorated, the fiber sheet 10bs may not be cut successfully, which may cause a plurality of the sheet fragments 10bh to be connected.

Next, a suction step is performed for sucking the sheet fragments 10bh, which have been obtained in the cutting step and are long in the first direction, and supplying the sheet fragments to inside the duct 3. The supplying portion 5 includes the suction nozzle 58 whose suction opening 581 is arranged below the second cutter roller 54—i.e., more toward the downstream side, in the second cutter roller 54's rotating direction (the direction of arrow R4), than the closest point between the second cutter roller 54 and the receiving roller 55—as illustrated in FIGS. 4 and 5. In the suction step, the sheet fragments 10bh cut and obtained by the second cutter roller 54 are sucked by using the suction nozzle 58. By arranging the suction opening 581 of the suction nozzle 58 below the second cutter roller 54—i.e., more toward the downstream side, in the second cutter roller 54's rotating direction R4, than the closest point between the second cutter roller 54 and the receiving roller 55—the plurality of sheet fragments 10bh cut and formed by the second cutter roller 54 and the receiving roller 55 can be sucked efficiently.

Figure 7:
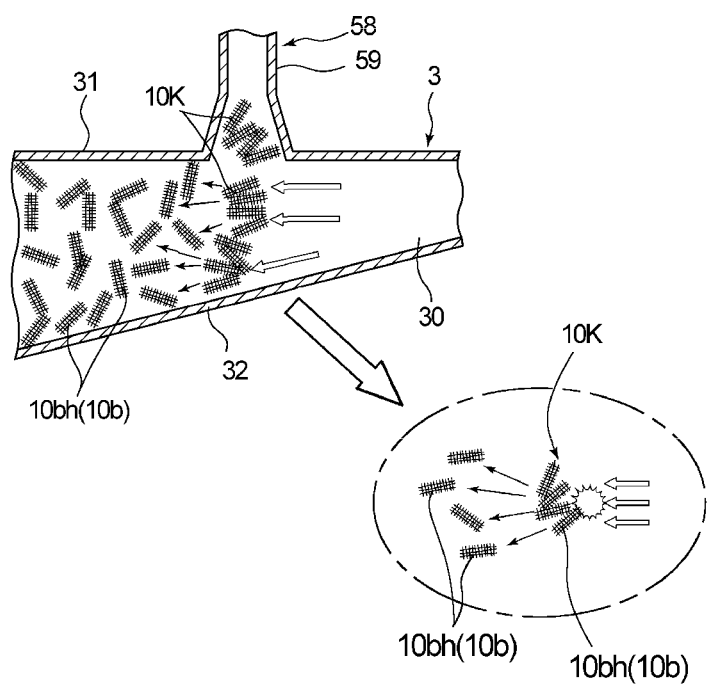
FIG. 7 is a schematic diagram illustrating a state where a cluster of sheet fragments collides against an airflow inside a duct and the sheet fragments are transported in a dispersed manner.

Next, a transporting step is performed for transporting the sheet fragments 10bh, which have been supplied to inside the duct 3, to the accumulating depression 41 on an airflow by using the duct 3. If, as described above, the sheet fragments 10bh have a fuzzy periphery or a plurality of sheet fragments 10bh are connected, when the sheet fragments 10bh are supplied to inside the duct 3, the fuzzy sheet fragments 10bh may be joined together and clusters 10K of sheet fragments 10bh may be formed, as illustrated in FIG. 7. So, in the transporting step, the sheet fragments 10bh are transported by an airflow created inside the duct 3 in a dispersed and airborne state to the accumulating depression 41 in the rotary drum 4's outer circumferential surface 4f. The sheet fragments 10bh sucked in the suction step are supplied to inside the duct 3 through the suction tube 59. Further, an airflow for transporting the materials of the absorbent member 100 toward the rotary drum 4's outer circumferential surface 4f is created in advance inside the duct 3's flow path 30. Thus, the plurality of sheet fragments 10bh are supplied to inside the duct 3 at a position in midstream of the flow direction of the airflow inside the duct 3.

As illustrated in FIG. 7, even if a cluster 10K of sheet fragments 10bh is inadvertently supplied, the velocity, toward the downstream side, of the airflow already flowing inside the duct 3's flow path 30 is greater than the velocity, toward the downstream side, of the plurality of sheet fragments 10bh supplied in midstream into the duct 3's flow path 30 through the suction tube 59; thus, when the cluster 10K of sheet fragments 10bh is supplied into the duct 3's flow path 30, the cluster 10K of sheet fragments 10bh collides against the already-flowing airflow. As illustrated in FIG. 7, due to the impact of contact with the airflow, in the cluster 10K of sheet fragments 10bh that has collided against the airflow, sections where the sheet fragments 10bh have joined together due to cutting failure or excessive tangling caused by the fuzz formed upon cutting are disentangled, and the cluster is separated into individual sheet fragments 10bh and transported in a dispersed and airborne state toward the downstream side. As described above, in the transporting step of the present embodiment, the sheet fragments 10bh are transported in a dispersed and airborne state by being separated into individual sheet fragments 10bh, and thus, an accumulation 100a' in which the sheet fragments 10bh are distributed uniformly can easily be manufactured stably.

The absorbent member 100 manufactured by the absorbent member manufacturing method includes hydrophilic fibers 10a. In the transporting step, the sheet fragments 10bh obtained in the cutting step and the hydrophilic fibers 10a obtained in the defibrating step are transported, while being mixed, to the accumulating depression 41. While being transported to the accumulating depression 41, the sheet fragments 10bh and the hydrophilic fibers 10a collide against one another in the airflow, thereby improving the dispersed and airborne state of the sheet fragments 10bh. Further, the sheet fragments 10bh and the hydrophilic fibers 10a are transported on the airflow in a dispersed and airborne state in which the sheet fragments and the hydrophilic fibers are mixed.

In the transporting step, the hydrophilic fibers 10a and the sheet fragments 10bh are supplied at mutually different positions along the flow direction of the airflow inside (in the flow path 30) of the duct 3. Further, the hydrophilic fibers 10a are transported by being supplied at a point more upstream, in the flow direction of the airflow, than the position where the sheet fragments 10bh are supplied. Stated differently, as illustrated in FIGS. 4 and 5, the defibrating machine 21 used for the defibrating step is arranged more toward the upstream side, in the duct 3, than the suction nozzle 58. In the transporting step, the hydrophilic fibers 10a obtained in the defibrating step are supplied into the duct 3's flow path 30 from the upstream side in the flow direction of the airflow in the duct 3, and the plurality of sheet fragments 10bh having undergone the suction step are supplied into the duct 3's flow path 30 in midstream of the duct 3. In the transporting step, the hydrophilic fibers 10a supplied from the defibrating machine 21 into the duct 3's flow path 30 are transported, by the airflow flowing inside the duct 3's flow path 30, toward the rotary drum 4's outer circumferential surface 4f from a point more upstream, in the flow direction of the airflow, than the position where the plurality of sheet fragments 10bh are supplied.

Figure 8:
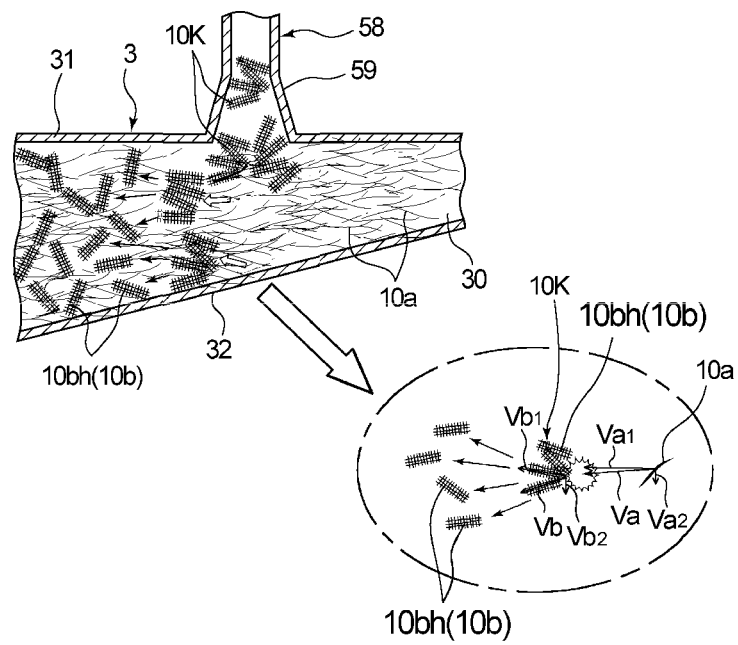
FIG. 8 is a schematic diagram illustrating a state where hydrophilic fibers collide against a cluster of sheet fragments inside the duct and the sheet fragments are transported in a dispersed manner.

Herein, in the transporting step, when the sheet fragments 10bh and the hydrophilic fibers 10a merge with one another inside the duct 3, the transportation velocity Vb of the sheet fragments 10bh is different from the transportation velocity Va of the hydrophilic fibers 10a. Moreover, the velocity component Va1, toward the downstream side, of the transportation velocity Va of the hydrophilic fibers 10a is greater than the velocity component Vb1, toward the downstream side, of the transportation velocity Vb of the sheet fragments 10bh. Note that the velocity component Va1, toward the downstream side, of the transportation velocity Va of the hydrophilic fibers 10a is the velocity component in the horizontal direction when the transportation velocity Va is divided into the horizontal-direction velocity component Va1 and the vertical-direction velocity component Va2 in a projected view when viewing the duct 3 from its side surface, as illustrated in FIG. 8. Similarly, the velocity component Vb1, toward the downstream side, of the transportation velocity Vb of the sheet fragments 10*bh* is the velocity component in the horizontal direction when the transportation velocity Vb is divided into the horizontal-direction velocity component Vb1 and the vertical-direction velocity component Vb2 in a projected view when viewing the duct 3 from its side surface, as illustrated in FIG. 8. In the transporting step, the hydrophilic fibers 10*a* are supplied from a point more upstream than the sheet fragments 10*bh*. Thus, when the sheet fragments 10*bh* and the hydrophilic fibers 10*a* merge with one another, the velocity component Va1, toward the downstream side, of the hydrophilic fibers 10*a* is greater than the velocity component Vb1, toward the downstream side, of the sheet fragments 10*bh*. Particularly, in the present embodiment, the sheet fragments 10*bh* are supplied to the duct 3's flow path 30 by the suction tube 59 which extends in a direction intersecting with the flow direction of the airflow in the duct 3. Thus, as regards the movement velocity of the sheet fragments 10*bh* immediately before being supplied to the duct 3's flow path 30, the velocity component toward the downstream side in the flow direction of the airflow inside the duct 3 does not become large. Therefore, the velocity component Va1, toward the downstream side in the flow direction of the airflow, of the transportation velocity Va of the hydrophilic fibers 10*a* is likely to become greater than the velocity component Vb1, toward the downstream side in the flow direction of the airflow, of the transportation velocity Vb of the sheet fragments 10*bh*. Thus, even if a cluster 10K of sheet fragments 10*bh* is inadvertently supplied into the duct 3's flow path 30, the cluster 10K of sheet fragments 10*bh* collides against the already-flowing hydrophilic fibers 10*a*. Then, as regards the cluster 10K of sheet fragments 10*bh* having collided against the hydrophilic fibers 10*a*, the tangling etc. caused by the fuzz formed upon cutting is further disentangled by the impact of contact with the hydrophilic fibers 10*a*, as illustrated in FIG. 8, and the cluster is separated into individual sheet fragments 10*bh* and transported in a dispersed and airborne state toward the downstream side. In the transporting step, collision between the cluster 10K of sheet fragments 10*bh* and the hydrophilic fibers 10*a* in the airflow further separates the individual sheet fragments 10*bh* and improves the dispersed and airborne state, and the hydrophilic fibers 10*a* and the sheet fragments 10*bh* are thus transported by the airflow in a dispersed and airborne state while being mixed. Thus, even if sheet fragments 10*bh* with a fuzzy periphery are formed or a plurality of sheet fragments 10*bh* are connected before being supplied to inside the duct 3, it is easy to stably manufacture an accumulation 100*a*' in which the sheet fragments 10*bh* and the hydrophilic fibers 10*a* are distributed uniformly.

Further, the absorbent member 100 manufactured by this method for manufacturing an absorbent member 100 includes absorbent particles 10*c* in addition to the hydrophilic fibers 10*a*. In the transporting step, in addition to the collision between the sheet fragments 10*bh* and the hydrophilic fibers 10*a*, the sheet fragments 10*bh* obtained in the cutting step and the absorbent particles 10*c* are caused to collide in the airflow while the sheet fragments 10*bh* and the absorbent particles 10*c* are being transported to the accumulating depression 41, thereby improving the dispersed and airborne state of the sheet fragments 10*bh*. Further, the sheet fragments 10*bh* and the absorbent particles 10*c* are transported by the airflow in a dispersed and airborne state in which the sheet fragments and the absorbent particles are mixed.

In the transporting step, the absorbent particles 10*c* and the sheet fragments 10*bh* are supplied at mutually different positions along the flow direction of the airflow. Further, the absorbent particles 10*c* are supplied at a point more upstream, in the flow direction, than the position where the sheet fragments 10*bh* are supplied. Stated differently, as illustrated in FIGS. 4 and 5, the absorbent particle dispersing tube 36 is arranged more toward the upstream side, in the duct 3, than the suction nozzle 58. In the transporting step, the absorbent particles 10*c* are supplied into the duct 3's flow path 30 from a more upstream point of the duct 3 than the suction nozzle 58, and the plurality of sheet fragments 10*bh* having undergone the suction step are supplied into the duct 3's flow path 30 at a more downstream point of the duct 3 than the arrangement position of the absorbent particle dispersing tube 36. In the transporting step, the absorbent particles 10*c* supplied from the absorbent particle dispersing tube 36 into the duct 3's flow path 30 are transported, by the airflow flowing inside the duct 3's flow path 30, toward the rotary drum 4's outer circumferential surface 4*f* from a point more upstream, in the flow direction of the airflow, than the position where the plurality of sheet fragments 10*bh* are supplied.

Figure 9:
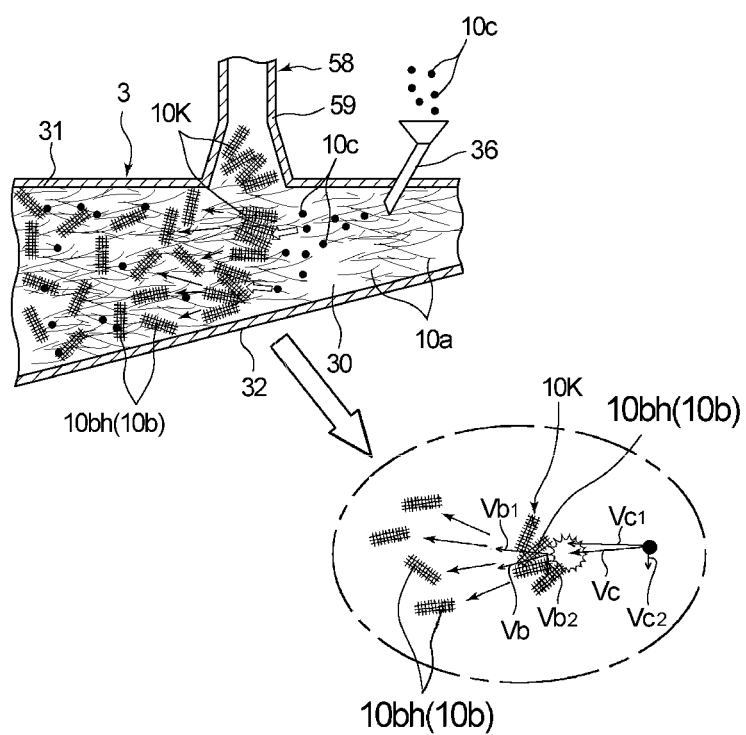
FIG. 9 is a schematic diagram illustrating a state where absorbent particles collide against a cluster of sheet fragments inside the duct and the sheet fragments are transported in a dispersed manner.

Herein, in the transporting step, when the sheet fragments 10*bh* and the absorbent particles 10*c* merge with one another, the transportation velocity Vb of the sheet fragments 10*bh* is different from the transportation velocity Vc of the absorbent particles 10*c*. Moreover, the velocity component Vc1, toward the downstream side, of the transportation velocity Vc of the absorbent particles 10*c* is greater than the velocity component Vb1, toward the downstream side, of the transportation velocity Vb of the sheet fragments 10*bh*. Note that the velocity component Vc1, toward the downstream side, of the transportation velocity Vc of the absorbent particles 10*c* is the velocity component in the horizontal direction when the transportation velocity Vc is divided into the horizontal-direction velocity component Vc1 and the vertical-direction velocity component Vc2 in a projected view when viewing the duct 3 from its side surface, as illustrated in FIG. 9. In the transporting step of the present embodiment, the absorbent particles 10*c* are supplied from a point more upstream than the sheet fragments 10*bh*. Thus, when the sheet fragments 10*bh* and the absorbent particles 10*c* merge with one another, the velocity component Vc1, toward the downstream side, of the absorbent particles 10*c* is greater than the velocity component Vb1, toward the downstream side, of the sheet fragments 10*bh*. Thus, if a cluster 10K of sheet fragments 10*bh* is supplied into the duct 3's flow path 30, the cluster 10K of sheet fragments 10*bh* collides against the already-flowing absorbent particles 10*c*. Then, as regards the cluster 10K of sheet fragments 10*bh* having collided against the absorbent particles 10*c*, the tangling etc. caused by the fuzz formed upon cutting is further disentangled by the impact of contact with the absorbent particles 10*c*, as illustrated in FIG. 9, and the cluster is separated into individual sheet fragments 10*bh* and transported in a dispersed and airborne state toward the downstream side. In the transporting step, the collision of the cluster 10K of sheet fragments 10*bh* against the hydrophilic fibers 10*a* in the airflow and also against the absorbent particles 10*c* further separates the individual sheet fragments 10*bh* and improves the dispersed and airborne state, and the hydrophilic fibers 10*a*, the sheet fragments 10*bh*, and the absorbent particles 10*c* are thus transported by the airflow in a dispersed and airborne state while being mixed. Thus, it is easy to stably manufacture an accumulation 100a' in which the hydrophilic fibers 10a, the sheet fragments 10bh, and the absorbent particles 10c are distributed uniformly. Particularly, since the absorbent particles 10c have a greater specific gravity than the sheet fragments 10bh, the sheet fragments 10bh are more easily separated into individual fragments.

Next, an accumulating step is performed for accumulating the sheet fragments 10bh transported in the transporting step in the accumulating depression 41, to form an accumulation 100a'. In the accumulating step, not only the sheet fragments 10bh but also the hydrophilic fibers 10a and the absorbent particles 10c are accumulated in the accumulating depression 41 arranged in the outer circumferential surface 4f of the rotary drum 4 to thereby form an accumulation 100a'. The sheet fragments 10bh, the hydrophilic fibers 10a, and the absorbent particles 10c are mixed while they are being transported toward the accumulating depression 41 in a dispersed and airborne state. Thus, in the accumulating depression 41, the sheet fragments 10bh are arranged in a dispersed state in the planar direction of the accumulating depression 41. Further, the sheet fragments 10bh, the hydrophilic fibers 10a, and the absorbent particles 10c accumulate in a mixed state in the thickness direction of the accumulating depression 41. The accumulation 100a' accumulated in the accumulating depression 41 as described above includes regions respectively having different quantities of sheet fragments 10bh overlapping one another over the entire region in the thickness direction, wherein such regions are present in a dispersed manner in both the longitudinal direction and the width direction of the accumulation 100a'.

Further, each sheet fragment 10bh is rectangular that is long in the first direction. Thus, in the transporting step, the sheet fragments 10bh are likely to be transported in a manner that the longitudinal direction (first direction) of each of the sheet fragments 10bh is oriented in the flow direction of the airflow when being transported in the transporting direction by the airflow. Further, in the accumulating step, the sheet fragments accumulate in the moving accumulating depression 41 while maintaining their orientation. Thus, it is easy to form an accumulation 100a' (see FIG. 1) in which the longitudinal direction (first direction) of the sheet fragments 10bh is oriented in the transporting direction Y of the accumulation 100a'. Herein, "the longitudinal direction of each of the sheet fragments 10bh is oriented in the flow direction of the airflow" means that the angle formed between the flow direction and the longitudinal direction of each sheet fragment 10bh is within a range that is less than 45 degrees. In the present embodiment, the absorbent member is manufactured such that the transporting direction Y is the longitudinal direction corresponding to the wearer's front-rear direction. Thus, it is easy to form an accumulation 100a' in which the longitudinal direction of each of the sheet fragments 10bh is oriented in the longitudinal direction of the absorbent member. When the longitudinal direction (first direction) of each sheet fragment 10bh is oriented in the transporting direction of the accumulation 100a' as described above, it is easy to form an accumulation 100a (see FIG. 1) in which the hydrophilic fibers 10a are linked together in the longitudinal direction of the absorbent member. When the hydrophilic fibers 10a are linked in the longitudinal direction, body fluid is easily diffused in the longitudinal direction in the manufactured absorbent member 100, and it becomes easy to use the entire surface of the absorbent member 100. In the accumulating step, it is preferable that the longitudinal direction of at least 50% of the sheet fragments 10bh present in the accumulation 100a' is oriented in the transporting direction of the accumulation 100a', and more preferable that the longitudinal direction of at least 70% of the sheet fragments 10bh present in the accumulation 100a' is oriented in the transporting direction of the accumulation 100a'. Herein, "the longitudinal direction of the sheet fragments 10bh is oriented in the transporting direction of the accumulation 100a'" means that the angle formed between the longitudinal direction of each sheet fragment 10bh and the transporting direction of the accumulation 100a' is within a range that is less than 45 degrees. It is preferable that the longitudinal direction of at least 50% of the sheet fragments 10bh included in the thus-formed accumulation 100a' is oriented in the longitudinal direction of the absorbent member 100, and more preferable that the longitudinal direction of at least 70% of the sheet fragments 10bh included in the accumulation 100a' is oriented in the longitudinal direction of the absorbent member 100.

In the manner described above, an accumulation 100a' in which the sheet fragments 10bh and the hydrophilic fibers are dispersed is formed within the accumulating depression 41 of the rotary drum 4. In the thus-formed accumulation 100a', the sheet fragments 10bh, which are larger than the hydrophilic fibers 10a, are accumulated in a dispersed manner in the longitudinal direction, which is one direction of the accumulation 100a', and the width direction (see FIG. 3). Thus, large gaps may be formed between adjacent sheet fragments 10bh. In the present manufacturing method, the accumulation 100a' formed in the accumulating depression 41 is formed continuously over the entire circumference, in the circumferential direction (2Y direction), of the rotary drum 4. After forming this accumulation 100a' in which the hydrophilic fibers 10a, the synthetic fibers 10b, and the absorbent particles 10c have accumulated within the accumulating depression 41, the rotary drum 4 is further rotated, and, while pressing down the accumulation 100a' in the accumulating depression 41 by the press-down belt 7 which is arranged on the outer circumferential surface 4f located at the space B of the rotary drum 4, the accumulation is transported to above the vacuum conveyor 8, as illustrated in FIG. 4.

Next, the covering step is performed, wherein: the accumulation 100a' obtained in the accumulating step is placed on the core-wrap sheet 100b which is continuous and is being transported; and the accumulation 100a' is covered with the core-wrap sheet 100b by folding back the core-wrap sheet 100b's both lateral sides, which extend along the transporting direction Y, in a manner that the core-wrap sheet's both lateral sides respectively cover at least both lateral sides, which extend along the transporting direction Y, of the accumulation 100a' placed on the core-wrap sheet. As illustrated in FIGS. 4 and 5, when the accumulation 100a' in the accumulating depression 41 reaches a position opposing the vacuum box 84 located at the space C of the rotary drum 4, the accumulation is released from the accumulating depression 41 by suction from the vacuum box 84. The accumulation 100a' released from the accumulating depression 41 is placed on one surface of the continuous core-wrap sheet 100b being transported by the vacuum conveyor 8. In this way, the accumulation 100a', which extends continuously along the transporting direction, is placed onto the central section, in the width direction, of the core-wrap sheet 100b. Then, as illustrated in FIG. 4, one lateral side of the core-wrap sheet 100b, of the two lateral sides which extend along the transporting direction, is folded inward in the width direction onto the accumulation 100a' by a folding guide plate (not illustrated), and the other lateral side is folded inward in the width direction onto the accumulation 100a' by a folding guide plate. In the present covering step, the covering step is performed in this way, wherein a continuous absorbent member precursor 101 is formed by covering the accumulation 100a' with the core-wrap sheet 100b.

From the viewpoint of causing the longitudinal direction (Y direction) of the sheet fragments 10bh to be oriented in the transporting direction of the accumulation 100a', it is preferable that, in the covering step, the accumulation 100a' placed on one surface of the core-wrap sheet 100b is transported in the transporting direction together with the core-wrap sheet 100b in a state where tension is applied in the transporting direction of the core-wrap sheet 100b. By being transported with a tension applied thereto in the transporting direction of the core-wrap sheet 100b, the accumulation 100a' will be stretched in the transporting direction; at this time, the regions in which the number of sheet fragments 10bh is relatively large and the number of hydrophilic fibers 10a is small—i.e., the regions in which linking among the hydrophilic fibers 10a is weak—are mainly stretched. Thus, the density of presence of the hydrophilic fibers 10a becomes even lower in these regions. As a result, it becomes easy to form a sparse-dense structure with an even greater density difference in the pressing step described below.

Next, the pressing step is performed for pressing the accumulation 100a' over its entirety in the thickness direction. In the present embodiment, the continuous absorbent member precursor 101, which is made by covering the accumulation 100a' with the core-wrap sheet 100b, is introduced between the pair of flat rollers 701a, 701b of the pressing portion 700, and the absorbent member precursor 101 is pressed over its entirety in the thickness direction. In the pressing step, the precursor 101, while being transported, is pressed along the transporting direction and is also pressed over the entire region in the width direction. As described above, in the precursor 101 before being pressed, there may be large gaps formed between adjacent sheet fragments 10bh within the accumulation 100a' (see FIG. 3). By pressing the precursor 101 in the pressing step in the thickness direction (Z direction), the large gaps collapse, thereby making it easy to form an accumulation 100a in which the gaps among the constituent fibers are substantially uniform. Thus, it is possible to reduce large gaps of sizes that inhibit spreading of body fluid when the absorbent member absorbs body fluid, and thus manufacture an absorbent member having excellent absorbency.

From the viewpoint of forming a closely packed sparse-dense structure by orienting the sheet fragments 10bh in the transporting direction of the accumulation 100a' and uniformly pressing the entire precursor 101, it is preferable that, in the pressing step, the precursor 101 is pressed in a state where, while transporting the precursor, tension is applied thereto in the transporting direction.

Further, in cases of forming, in the accumulating step, an accumulation 100a' that includes regions respectively having different quantities of the sheet fragments 10bh overlapping one another over the entire region in the thickness direction of the accumulation 100a', and in which such regions are present in a dispersed manner in the longitudinal direction and the width direction of the accumulation 100a', it is preferable that pressing is performed in the pressing step with a pressurization force of a degree capable of forming a sparse-dense structure. By performing pressing in this way, regions in which the number of sheet fragments 10bh is relatively large and the number of hydrophilic fibers 10a is small become sparse regions, whereas regions in which the number of sheet fragments 10bh is relatively small and the number of hydrophilic fibers 10a is large become dense regions, and thus, the accumulation 100a is provided with a sparse-dense structure in which there is a distribution in density of presence of the hydrophilic fibers 10a and the sheet fragments 10bh including the synthetic fibers 10b.

Note that, from the viewpoint of achieving a balance between the formation of an effective sparse-dense structure and the hardness of the absorbent member, it is preferable to press the precursor 101 in the pressing step by adjusting the distance between the pair of pressing rollers 701a, 701b in accordance with the thickness of the precursor 101 by using a distance adjusting device (not illustrated). It is preferable that the percentage of the distance (701d) between the pair of pressing rollers 701a, 701b to the thickness (101t) of the precursor 101 ((701d/101t)×100; see FIG. 5) is preferably 1% or greater, more preferably 5% or greater, and preferably 50% or less, more preferably 30% or less, and preferably from 1 to 50%, more preferably from 5 to 30%.

Then, the continuous absorbent member is cut at predetermined intervals in the transporting direction with a cutting device (not illustrated), to thereby manufacture separate absorbent members 100. Each absorbent member 100 manufactured as above has a sparse-dense structure wherein the gaps formed among the sheet fragments 10bh are small and the gaps are substantially uniform, as illustrated in FIG. 2. By using an absorbent article including such an absorbent member 100, absorbency is improved, since body fluid can be absorbed quickly by the sparse-structure section and body fluid can be diffused by the dense-structure section.

Note that the method for manufacturing the absorbent member 100 preferably includes, before the aforementioned cutting step, a heating step of heating the fiber sheet 10bs and making the sheet's thickness thicker than the sheet's thickness before heating. For example, in the heating step, the fiber sheet 10bs is subjected to a heating treatment by blowing hot air or water vapor thereon by using a heating portion including: a heating zone (not illustrated) including a heating blower (not illustrated) and a hot-air suction box (not illustrated); and a cooling zone (not illustrated). By performing this heating step, sheet fragments 10bh with an increased thickness can be formed in the cutting step, and thus, regions with even fewer hydrophilic fibers 10a can be formed in the accumulating step. By pressing the thus-manufactured accumulation 100a' in the thickness direction, a sparse-dense structure having an even greater difference between sparse and dense regions can be formed easily.

The thickness of the fiber sheet 10bs is measured according to the following method.

For example, a sample having a predetermined area is cut out from the fiber sheet 10bs, and, in a state where a load of 0.05 kPa is applied thereto, the thickness is measured with a thickness measurement instrument. For example, a laser displacement meter from Omron Corporation can be used for the thickness measurement instrument. The thickness is measured at ten points, and the average value thereof is calculated as the thickness of the fiber sheet 10bs. Alternatively, the cross section of the cut-out sample may be magnified with a digital microscope etc., and the thickness of the fiber sheet 10bs may be measured. Note, however, that the method is not limited to the above, and it is preferable that, even when measured according to other measurement methods, the thickness of the fiber sheet 10bs having undergone the heating treatment has a greater thickness than the thickness of the fiber sheet 10bs before being heated.

From the viewpoint of heating the fiber sheet 10bs efficiently, it is preferable that the hot air or the water vapor to be blown by the heating blower of the heating portion has a temperature that is preferably equal to or higher than the glass transition point $T_g$ of the synthetic fibers 10b constituting the fiber sheet 10bs, and more preferably at least 3° C. higher than the $T_g$. The upper limit of the temperature of the hot air or the water vapor to be blown is preferably below the melting point $T_m$ of the synthetic fibers 10b constituting the fiber sheet 10bs, and more preferably at least 3° C. lower than the $T_m$.

The present invention is not limited to the foregoing embodiments and can be modified as appropriate.

For example, the aforementioned method for manufacturing the absorbent member 100 includes a covering step of covering the formed accumulation 100a' with a core-wrap sheet 100b and forming a precursor 101 of the absorbent member 100, but the covering step does not have to be provided. In cases where there is no covering step, the formed accumulation 100a' may be directly pressed in the pressing step over its entirety in the thickness direction.

Further, in the method for manufacturing the absorbent member 100, the entire precursor 101 is pressed in the thickness direction by using the pressing portion 700 including the pair of flat rollers 701a, 701b. However, instead of using the pair of flat rollers 701a, 701b, the precursor 101 may be pressed by using a pressing means such as a pair of pressing plates or a pair of conveyor belts.

Further, the method for manufacturing the absorbent member 100 involves a defibrating step of defibrating the continuous hydrophilic sheet 10as by using the defibrating machine 21 and obtaining the hydrophilic fibers 10a, but the defibrating step does not have to be provided. Further, in the method for manufacturing the absorbent member 100, the absorbent particles 10c are supplied by using the absorbent particle dispersing tube 36, but the absorbent particles 10c do not have to be supplied.

Further, as illustrated in FIG. 4, in the cutting step of the present embodiment, sheet fragments 10bh having the same size are manufactured by cutting the fiber sheet 10bs by using the first cutter roller 53 and the second cutter roller 54, but instead, a cutter mill-type pulverizing device may be used. However, in cases of forming sheet fragments by using a cutter mill system, it is difficult to form sheet fragments that all have a fixed size, and there are variations with respect to the intended size. When there are variations in the size of the sheet fragments, unevenness arises in the size of the gaps formed in the absorbent member, which may lead to unevenness in absorbency when the absorbent member absorbs body fluid. Thus, it is preferable to form the sheet fragments 10bh by cutting the fiber sheet 10bs at predetermined lengths in the first direction and the second direction.

Further, instead of using cutter rollers, the sheet fragments 10bh may be formed by cutting the fiber sheet 10bs by using a press machine including cutter blades 51 that cut in the first direction (Y direction) and a press machine including cutter blades 52 that cut in the second direction (X direction).

Further, the cutting step of the present embodiment employs the first cutter roller 53 and the second cutter roller 54 as illustrated in FIG. 4. Instead of the two cutter rollers, it is possible to use a single cutter roller having, on the same circumferential surface, cutter blades 51 that cut in the first direction and cutter blades 52 that cut in the second direction.

The shape of the accumulation 100a to be manufactured may be changed flexibly by changing the shape of the accumulating depression 41. Further, the fibers used for the synthetic fibers 10b may be subjected to a hydrophilizing treatment.

In relation to the foregoing embodiments, the following absorbent member manufacturing methods are further disclosed.

{1}

A method for manufacturing an absorbent member including synthetic fibers, the method comprising:

a transporting step of transporting a plurality of sheet fragments including synthetic fibers to an accumulating portion by using a transporting portion;

an accumulating step of accumulating, in the accumulating portion, the plurality of sheet fragments transported in the transporting step, and forming an accumulation which is a constituent member of the absorbent member; and a pressing step of pressing the accumulation over its entirety in a thickness direction.

{2}

The method for manufacturing an absorbent member as set forth in clause {1}, wherein:

the method further comprises a defibrating step of defibrating a continuous hydrophilic sheet and obtaining hydrophilic fibers;

in the transporting step, the plurality of sheet fragments and the hydrophilic fibers obtained in the defibrating step are transported to the accumulating portion while being mixed; and in the accumulating step, the accumulation is formed by accumulating the sheet fragments and the hydrophilic fibers in the accumulating portion.

{3}

The method for manufacturing an absorbent member as set forth in clause {2}, wherein:

in the accumulating step, the accumulation is formed, wherein the accumulation includes regions respectively having different quantities of the sheet fragments overlapping one another over an entire region, in the thickness direction, of the accumulation, and such regions are present in a dispersed manner in a longitudinal direction of the accumulation and a lateral direction orthogonal to the longitudinal direction; and in the pressing step, the accumulation is pressed, to form an absorbent member in which there is a distribution in density of presence of the hydrophilic fibers in both the longitudinal direction and the lateral direction of the accumulation.

{4}

The method for manufacturing an absorbent member as set forth in any one of clauses {1} to {3}, wherein:

a pair of flat rollers is used in the pressing step; and the accumulation is pressed by adjusting a distance between the pair of flat rollers to 50% or less with respect to the thickness of the accumulation.

{5}

The method for manufacturing an absorbent member as set forth in any one of clauses {1} to {4}, wherein:

a pair of flat rollers is used in the pressing step; and the percentage of the distance between the pair of pressing rollers to the thickness of the accumulation is preferably 1% or greater, more preferably 5% or greater, and preferably 50% or less, more preferably 30% or less, and preferably from 1 to 50%, more preferably from 5 to 30%.

{6}

The method for manufacturing an absorbent member as set forth in any one of clauses {1} to {4}, wherein, in the pressing step, the accumulation is pressed in a state where, while transporting the accumulation, tension is applied thereto in a transporting direction.

{7}

The method for manufacturing an absorbent member as set forth in any one of clauses {1} to {5}, wherein:

the method further comprises a cutting step of cutting a continuous fiber sheet including the synthetic fibers at predetermined lengths in a first direction and a second direction intersecting with the first direction, and forming the sheet fragments; and in the accumulating step, the accumulation is formed by accumulating the plurality of sheet fragments formed in the cutting step.

{8}

The method for manufacturing an absorbent member as set forth in clause {7}, wherein, in the cutting step:

continuous sheet fragment strips are formed by cutting the continuous fiber sheet by using a first cutter roller including cutter blades that cut in the first direction; and the plurality of sheet fragments are formed by cutting the continuous sheet fragment strips by using a second cutter roller including cutter blades that cut in the second direction.

{9}

The method for manufacturing an absorbent member as set forth in clause {7} or {8}, wherein the first direction is a direction in which the continuous fiber sheet is transported in the cutting step, and the second direction is a direction orthogonal to the first direction.

{10}

The method for manufacturing an absorbent member as set forth in any one of clauses {7} to {9}, wherein an average length of the sheet fragments formed in the cutting step is preferably from 0.3 to 30 mm, more preferably from 1 to 15 mm, even more preferably from 2 to 10 mm.

{11}

The method for manufacturing an absorbent member as set forth in any one of clauses {7} to {10}, wherein an average width of the sheet fragments formed in the cutting step is preferably from 0.1 to 10 mm, more preferably from 0.3 to 6 mm, even more preferably from 0.5 to 5 mm.

{12}

The method for manufacturing an absorbent member as set forth in any one of clauses {7} to {11}, wherein:

the method further comprises a heating step of heating the continuous fiber sheet and making the sheet's thickness thicker than the sheet's thickness before heating; and in the cutting step, the sheet fragments are formed by cutting the continuous fiber sheet having been heated by the heating step.

{13}

The method for manufacturing an absorbent member as set forth in clause {12}, wherein, in the heating step, the continuous fiber sheet is heated by blowing hot air or water vapor thereon.

{14}

The method for manufacturing an absorbent member as set forth in clause {13}, wherein the hot air or the water vapor has a temperature that is preferably equal to or higher than the glass transition point $T_g$ of the synthetic fibers constituting the fiber sheet, more preferably at least 3° C. higher than the $T_g$, and preferably below the melting point $T_m$ of the synthetic fibers constituting the fiber sheet, more preferably at least 3° C. lower than the $T_m$.

{15}

The method for manufacturing an absorbent member as set forth in any one of clauses {1} to {16}, wherein, in the transporting step, the plurality of sheet fragments are transported by an airflow created within the transporting portion.

{16}

The method for manufacturing an absorbent member as set forth in clause {15}, wherein:

the sheet fragments that are used have a rectangular shape that is long in one direction; and in the transporting step, the sheet fragments are transported in a manner that a longitudinal direction of each of the sheet fragments is oriented in a flow direction of the airflow.

{17}

The method for manufacturing an absorbent member as set forth in clause {16}, wherein, in the accumulating step, the accumulation is formed by accumulating the sheet fragments in the accumulating portion in a manner that the longitudinal direction of at least 50% of the sheet fragments present in the accumulation is oriented in the transporting direction of the accumulation.

{18}

The method for manufacturing an absorbent member as set forth in clause {17}, wherein, in the accumulating step, it is preferable that the longitudinal direction of at least 50% of the sheet fragments present in the accumulation is oriented in the transporting direction of the accumulation, and more preferable that the longitudinal direction of at least 70% of the sheet fragments present in the accumulation is oriented in the transporting direction of the accumulation.

{19}

The method for manufacturing an absorbent member as set forth in clause {17} or {18}, wherein, in the accumulating step, it is preferable that the longitudinal direction of at least 50% of the sheet fragments included in the accumulation is oriented in the longitudinal direction of the absorbent member, and more preferable that the longitudinal direction of at least 70% of the sheet fragments included in the accumulation is oriented in the longitudinal direction of the absorbent member.

{20}

The method for manufacturing an absorbent member as set forth in any one of clauses {1} to {19}, wherein the method further comprises a covering step of covering the accumulation formed in the accumulating step with a core-wrap sheet.

{21}

The method for manufacturing an absorbent member as set forth in clause {20}, wherein, in the covering step:

the accumulation is placed on the core-wrap sheet which is continuous and is being transported; and the accumulation is covered with the core-wrap sheet by folding back the core-wrap sheet's both lateral sides which extend along the transporting direction in a manner that the core-wrap sheet's both lateral sides, which extend along the transporting direction, respectively cover at least both lateral sides, which extend along the transporting direction, of the accumulation placed on the core-wrap sheet.

{22}

The method for manufacturing an absorbent member as set forth in clause {21}, wherein, in the covering step, the accumulation placed on a surface of the core-wrap sheet is transported together with the core-wrap sheet in a state where tension is applied in the transporting direction of the core-wrap sheet.

{23}

The method for manufacturing an absorbent member as set forth in any one of clauses {20} to {22}, wherein, in the pressing step, the accumulation covered with the core-wrap sheet is pressed.

INDUSTRIAL APPLICABILITY

According to the present invention, it is possible to manufacture an absorbent member with excellent absorbency.

The invention claimed is:

1. A method for manufacturing an absorbent member including synthetic fibers, the method comprising:
 a defibrating step of defibrating a continuous hydrophilic sheet and obtaining hydrophilic fibers;
 a transporting step of transporting a plurality of sheet fragments, which comprise synthetic fibers, to an accumulating portion by using a transporting portion, and in the transporting step, the plurality of sheet fragments and the hydrophilic fibers obtained in the defibrating step are transported to the accumulating portion while being mixed;
 an accumulating step of accumulating, in the accumulating portion, the plurality of sheet fragments transported in the transporting step, and forming an accumulation which is a constituent member of the absorbent member; and
 a pressing step of pressing the accumulation over its entirety in a thickness direction;
 wherein in the accumulating step, the accumulation is formed by accumulating the sheet fragments and the hydrophilic fibers in the accumulating portion, and
 wherein the accumulation includes regions respectively having different quantities of the sheet fragments overlapping one another over an entire region, in the thickness direction, of the accumulation, and the regions are present in a dispersed manner in a longitudinal direction of the accumulation and a lateral direction orthogonal to the longitudinal direction; and
 wherein in the pressing step, the accumulation is pressed, to form an absorbent member in which there is a distribution in density of presence of the hydrophilic fibers in both the longitudinal direction and the lateral direction of the accumulation.

2. The method for manufacturing an absorbent member according to claim 1, wherein, in the pressing step, the accumulation is pressed in a state where, while transporting the accumulation, tension is applied thereto in a transporting direction.

3. The method for manufacturing an absorbent member according to claim 1, wherein:
 the method further comprises a cutting step of cutting a continuous fiber sheet including the synthetic fibers at predetermined lengths in a first direction and a second direction intersecting with the first direction, and forming the sheet fragments; and
 the accumulating step, the accumulation is formed by accumulating the plurality of sheet fragments formed in the cutting step.

4. The method for manufacturing an absorbent member according to claim 3, wherein, in the cutting step:
 continuous sheet fragment strips are formed by cutting the continuous fiber sheet by using a first cutter roller including cutter blades that cut in the first direction; and
 the plurality of sheet fragments are formed by cutting the continuous sheet fragment strips by using a second cutter roller including cutter blades that cut in the second direction.

5. The method for manufacturing an absorbent member according to claim 4, wherein an average length of the sheet fragments formed in the cutting step is from 0.3 to 30 mm.

6. The method for manufacturing an absorbent member according to claim 4, wherein an average width of the sheet fragments formed in the cutting step is from 0.1 to 10 mm.

7. The method for manufacturing an absorbent member according to claim 3, wherein the first direction is a direction in which the continuous fiber sheet is transported in the cutting step, and the second direction is a direction orthogonal to the first direction.

8. The method for manufacturing an absorbent member according to claim 3, wherein:
 the method further comprises a heating step of heating the continuous fiber sheet and making the sheet's thickness thicker than the sheet's thickness before heating; and
 in the cutting step, the sheet fragments are formed by cutting the continuous fiber sheet having been heated by the heating step.

9. The method for manufacturing an absorbent member according to claim 8, wherein, in the heating step, the continuous fiber sheet is heated by blowing hot air or water vapor thereon.

10. The method for manufacturing an absorbent member according to claim 9, wherein the hot air or the water vapor has a temperature that is equal to or higher than the glass transition point Tg of the synthetic fibers constituting the fiber sheet and below the melting point Tm thereof.

11. The method for manufacturing an absorbent member according to claim 1, wherein, in the transporting step, the plurality of sheet fragments are transported by an airflow created within the transporting portion.

12. The method for manufacturing an absorbent member according to claim 11, wherein:
 the sheet fragments that are used have a rectangular shape that is long in one direction; and
 in the transporting step, the sheet fragments are transported in a manner that a longitudinal direction of each of the sheet fragments is oriented in a flow direction of the airflow.

13. The method for manufacturing an absorbent member according to claim 12, wherein, in the accumulating step, the accumulation is formed by accumulating the sheet fragments in the accumulating portion in a manner that the longitudinal direction of at least 50% of the sheet fragments present in the accumulation is oriented in the transporting direction of the accumulation.

14. The method for manufacturing an absorbent member according to claim 13, wherein the longitudinal direction of at least 50% of the sheet fragments included in the accumulation is oriented in a longitudinal direction of the absorbent member.

15. The method for manufacturing an absorbent member according to claim 1, wherein the method further comprises a covering step of covering the accumulation formed in the accumulating step with a core-wrap sheet.

16. The method for manufacturing an absorbent member according to claim 15, wherein, in the covering step:
 the accumulation is placed on the core-wrap sheet which is continuous and is being transported; and
 the accumulation is covered with the core-wrap sheet by folding back the core-wrap sheet's both lateral sides which extend along the transporting direction in a manner that the core-wrap sheet's both lateral sides, which extend along the transporting direction, respectively cover at least both lateral sides, which extend along the transporting direction, of the accumulation placed on the core-wrap sheet.

17. The method for manufacturing an absorbent member according to claim 16, wherein, in the covering step, the accumulation placed on a surface of the core-wrap sheet is transported together with the core-wrap sheet in a state where tension is applied in the transporting direction of the core-wrap sheet.

18. The method for manufacturing an absorbent member according to claim 15, wherein, in the pressing step, the accumulation covered with the core-wrap sheet is pressed.

* * * * *